United States Patent
Levêque

(10) Patent No.: US 11,027,083 B2
(45) Date of Patent: Jun. 8, 2021

(54) PRESSURE REGULATOR FOR ENDOTRACHEAL TUBE CUFF, BREATHING SYSTEM COMPRISING SUCH A REGULATOR AND CONTAINER COMPRISING A VARIABLE VOLUME CHAMBER FOR SUCH A REGULATOR

(71) Applicant: LEVED, Paris (FR)

(72) Inventor: Edouard Levêque, Paris (FR)

(73) Assignee: LEVED, Paris (FR)

( * ) Notice: Subject to any disclaimer, the term of this patent is extended or adjusted under 35 U.S.C. 154(b) by 329 days.

(21) Appl. No.: 16/151,913

(22) Filed: Oct. 4, 2018

(65) Prior Publication Data

US 2019/0105451 A1 Apr. 11, 2019

(30) Foreign Application Priority Data

Oct. 9, 2017 (EP) .................................... 17195526

(51) Int. Cl.
*A61M 16/04* (2006.01)
*A61M 16/00* (2006.01)

(52) U.S. Cl.
CPC ...... *A61M 16/044* (2013.01); *A61M 16/0003* (2014.02); *A61M 2016/0027* (2013.01);
(Continued)

(58) Field of Classification Search
CPC . A61M 16/00–0012; A61M 2016/0015–0042; A61M 2016/04–0497;
(Continued)

(56) References Cited

U.S. PATENT DOCUMENTS 4,476,725 A * 10/1984 Chorel .................. G01L 9/0022
73/704
2011/0109458 A1 5/2011 Shipman

FOREIGN PATENT DOCUMENTS

EP 0489516 6/1992
FR 2940621 7/2010
(Continued)

OTHER PUBLICATIONS

Duguet et al., "Control of tracheal cuff pressure: a pilot study using a pneumatic device," Intensive Care Med., 33:128-132 (2007).
(Continued)

*Primary Examiner* — Jan Christopher L Merene
*Assistant Examiner* — Ned T Heffner
(74) *Attorney, Agent, or Firm* — Barnes & Thornburg LLP; G. Peter Nichols

(57) ABSTRACT

A pressure regulator includes a container defining a variable volume chamber having a least one first orifice to be connected to an auxiliary hose such that, in use, the variable volume chamber of the pressure regulator and a sealing cuff are in communication. The regulator includes a pressure means acting on the container for exerting a certain force by means of a weight that can move along an articulated rod for adjusting the air pressure contained in the variable volume chamber. A system for locking the weight is provided for preventing unexpected movement of the weight. The invention is applicable to endotracheal tubes, tracheotomy tube or similar instruments for the ventilation of a patient.

10 Claims, 4 Drawing Sheets

(52) U.S. Cl.
CPC . *A61M 2205/273* (2013.01); *A61M 2205/276* (2013.01); *A61M 2205/502* (2013.01); *A61M 2205/52* (2013.01); *A61M 2205/583* (2013.01); *A61M 2205/584* (2013.01)

(58) Field of Classification Search
CPC ........... A61M 2016/06; A61M 2016/08–0891; A61M 2016/16–168; A61M 2016/20; A61M 2016/208; A61M 25/10; A61M 25/1018–10188; G05D 16/00–0402; G05D 16/06; G05D 16/0608–08
See application file for complete search history.

(56) References Cited

FOREIGN PATENT DOCUMENTS

| | | |
|---|---|---|
| WO | WO 99/33508 | 7/1999 |
| WO | WO 99/40960 | 8/1999 |
| WO | WO 02/074376 | 9/2002 |
| WO | WO 2013/102905 | 7/2013 |
| WO | WO 2013/139986 | 9/2013 |

OTHER PUBLICATIONS

Search Report issued in EP application No. 17195526 (2018).

\* cited by examiner

PRESSURE REGULATOR FOR ENDOTRACHEAL TUBE CUFF, BREATHING SYSTEM COMPRISING SUCH A REGULATOR AND CONTAINER COMPRISING A VARIABLE VOLUME CHAMBER FOR SUCH A REGULATOR

CROSS REFERENCE TO RELATED APPLICATIONS

This application claims priority to European Patent Application No. 17195526.3, filed Oct. 9, 2017; the entirety of which is incorporated herein by reference.

BACKGROUND

Any patient who undergoes a general anesthesia, who is in a comatose state or who suffers from respiratory insufficiency must be ventilated. For this, a machine known as a "respirator" or "ventilation machine" is usually used, the function of which is to send a pressurized mixture of oxygen and carbon dioxide, optionally mixed with an anesthetic gas, into the lungs of the patient. The gaseous mixture and the machine will compensate for the muscle movements that enable the patient to breathe in and breathe out.

The gaseous mixture may be insufflated into the trachea artery of the patient by means of a pipe (main pipe) which passes either through the mouth, or through the nose of the patient and which is usually known as an "endotracheal tube" or "endonasal tube" as appropriate. If the patient must be ventilated over a long period (more than two weeks) or if the intubation is rendered impossible due to anatomical or facial trauma problems, the surgeons usually use a "tracheotomy tube". The tube, more or less rigid, of angled shape, consists of, like the aforementioned endotracheal tubes, a pipe (main pipe) which is inserted into the trachea artery of the patient by making an opening in the trachea (tracheotomy).

When the patient is ventilated by an endotracheal tube or a tracheotomy tube, the access through which the gaseous mixture is sent must be hermetically sealed so that same can inflate the thoracic cage of the patient and remain in the lungs thereof long enough so that the oxygen/carbon dioxide exchange is performed. For this, the main pipe of the tracheotomy tube or of the endotracheal tube is usually provided, in the region of the end thereof which is inserted into the trachea artery, with a small inflatable annular balloon, known as a "cuff" that surrounds the aforementioned end of the main pipe. Once the endotracheal tube or tracheotomy tube has been put in place, the cuff is inflated with air using a small hose (auxiliary hose) which is partially embedded in the material of the main pipe and which enables the passage of air between the cuff and the exterior. The outer end of the auxiliary hose is usually provided with a valve (check valve), to which can be connected a compressed air source, such as, for example, a manually operable rubber bulb or a syringe for inflating the cuff. The valve prevents the air from coming out of the cuff after same has been inflated and after the rubber inflation bulb or syringe has been removed. In order to fulfill the sealing function thereof, the cuff must have a suitable internal pressure so that it is hermetically pressed against the trachea artery of the patient in order to retain the mixture insufflated into the lungs throughout the insufflation time. In addition, if the cuff is not inflated enough, secretions may move down to the lungs and thus lead to risks of infections. Thus, it is essential for the cuff to be correctly pressed against the tracheal wall.

However, the pressure that the cuff of the endotracheal tube or tracheotomy tube exerts on the tracheal wall is not inconsequential. Indeed, any continuous pressure on any part of the human body interferes with the blood flow in the affected part. If the pressure exerted by the cuff on the tracheal wall is too high, the pressure will prevent the blood flow in the area of the tracheal wall that is in contact with the cuff. This lack of blood flow, if prolonged, may lead to a necrosis of the aforementioned area of the trachea. The necrosis may itself cause stenosis of the trachea, that is to say that the diameter thereof shrinks and that the trachea tightens around the cuff. Although air is a compressible element, in the event of stenosis and for each fluctuation of the diameter of the trachea (during each insufflation and exsufflation), overpressure is produced inside the cuff which interferes with the blood flow of the tissues in the area of the trachea. Indeed, the volume of air contained in the cuff opposes a resistance to tightening of the trachea and the resistance results in increased pressure of the cuff against the tracheal wall, which amplifies the non-vascularization phenomenon, thus the risks of necrosis and stenosis.

On the other hand, during a general anesthesia, the gas used for the anesthesia, usually nitrogen oxide, has a molecular composition such that the gas insufflated by the main pipe into the lungs may migrate into the sealing cuff through the wall thereof. By returning into the cuff, the gas increases the volume of the latter and the increase in volume causes an increase in the pressure exerted by the cuff on the trachea. Again, there is thus a risk of lack of vascularization of the area of the tracheal wall which is in contact with the cuff, hence a risk of necrosis and stenosis of the trachea.

When the cuffs are correctly inflated, the oro-pharyngeal secretions, not aspirated by the medical staff, are retained above the cuff which prevents them from moving down into the lungs.

However, during periods where the cuff is insufficiently inflated, the secretions above the cuff flow into the lungs. The repeated flows cause lung infections in the patients, which are the leading cause of death during intensive care.

In order to solve these problems, patent document WO 99/40960 proposes a pressure regulator for an endotracheal tube, a tracheotomy tube or similar instrument that makes it possible to maintain a constant and adjustable air pressure in the sealing cuff of the instrument and substantially constant but adjustable on a wall of the container for adjusting the air pressure contained in the variable volume chamber, and consequently the air pressure contained in the sealing cuff.

Such a pressure regulator has proven to be effective for maintaining the volume of the cuff in a sufficient way for maintaining the same pressed against the tracheal wall without taking the risk of causing an injury to the trachea. Indeed, it makes it possible to maintain a constant pressure in the cuff, the pressure being easily adjustable using a weight that can be moved along a rod pressing against the container filled with air and connected to the cuff. (See Doctor Duguet clinical trial, pulmonary resuscitation, Pitié-Salpétrière, Paris, France and published in November 2007 in the review "Intensive care medicine").

SUMMARY

The present invention relates to a pressure regulator for an endotracheal tube cuff, a tracheotomy tube or similar instrument for the ventilation of a patient. The instrument has a main pipe having a first end intended to be inserted into the trachea artery of a patient and a second end intended to be connected to a respirator apparatus, an inflatable annular sealing cuff, which surrounds the first end of the main pipe, and at least one auxiliary hose having a first end connected to the sealing cuff and a second end provided with a valve that can be connected to a compressed air source for inflating the sealing cuff.

The pressure regulator comprises a container defining a variable volume chamber having at least one first orifice to be connected to the auxiliary hose such that, in use, the variable volume chamber of the pressure regulator and the sealing cuff are in communication. The pressure regulator also includes a pressure means acting on the container for exerting a certain force by means of a weight that can move along an articulated rod for adjusting the air pressure contained in the variable volume chamber, and consequently the air pressure contained in the sealing cuff.

The invention also relates to a breathing system comprising such a regulator.

The invention also relates to a variable volume chamber suitable for such a regulator.

Also, the aim of the present invention is to propose a pressure regulator of the type for ensuring and maintaining a constant pre-set pressure in the cuff such as to protect, in particular, against unexpected manipulations that could occur with those close to the patient.

For this, such a regulator is remarkable in that it is provided with a system for locking the weight to prevent the unexpected movement thereof.

Additional objects, advantages, and novel features of the invention will be set forth in part in the description which follows, and in part will become apparent to those skilled in the art upon examination of the following, or may be learned from practice of the invention.

BRIEF DESCRIPTION OF THE DRAWINGS

The following description accompanies the drawings appended hereto, all given by way of non-limiting examples will be useful to understand how the invention may be embodied, on the drawings.

DESCRIPTION

Figure 1:
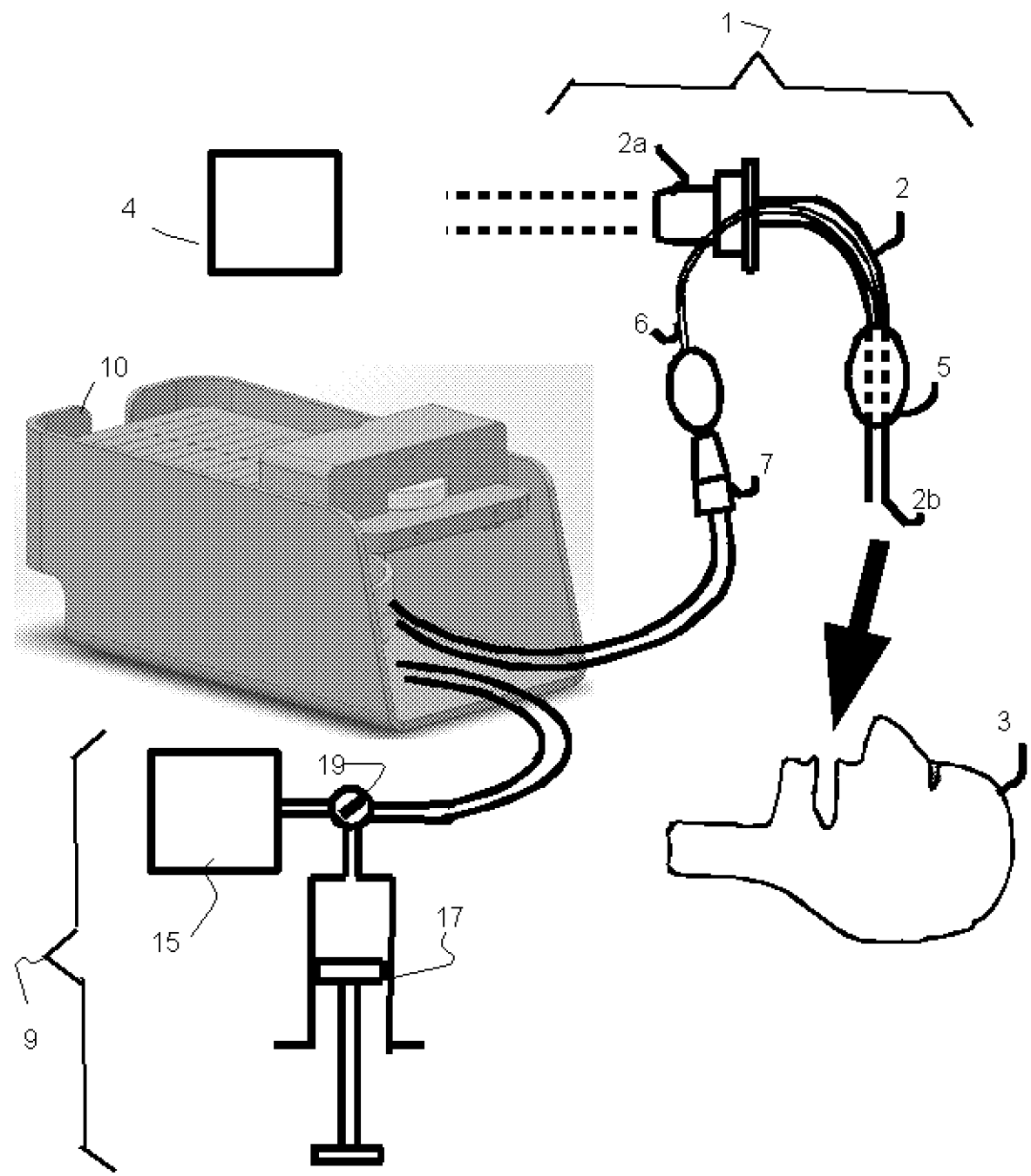
FIG. 1 represents a regulator according to the invention forming part of a breathing system.

As can be seen in FIG. 1, the tracheotomy tube 1 has a main pipe 2 in an arched shape made of a flexible elastomer material appropriate for medical or surgical use, a first end 2b of which is intended to be inserted into the trachea artery of a patient 3 and the second end 2a of which is intended to be connected to a respirator apparatus schematically represented by the block 4. In the region of the end 2b thereof, a sealing annular cuff 5 surrounds the first end 2b of the main pipe 2, the cuff being inflatable by means of a flexible auxiliary hose 6 having a first end connected to the sealing cuff 5 and a second end provided with a check valve 7 connected to a compressed air source 9, such as, for example, a manually operable pump, such as a rubber bulb, for inflating the cuff 5. The tube 1 is a well-known instrument, commercially available and which will not be described in greater detail.

The pressure regulator 10 is inserted between the compressed air source 9 and the auxiliary hose 6. The compressed air source may be formed of a compressed air generator 15 and a syringe 17. The auxiliary hose 6 is supplied from the elements 15 and 17 according to the control of a valve 19. The syringe 17 provides the air during the start-up of the regulator. The various connections are made using pipes of different colors.

According to one aspect of the invention, the regulator may be incorporated into a frame with the respirator apparatus 4 so as to form a compact breathing system.

Figure 2:
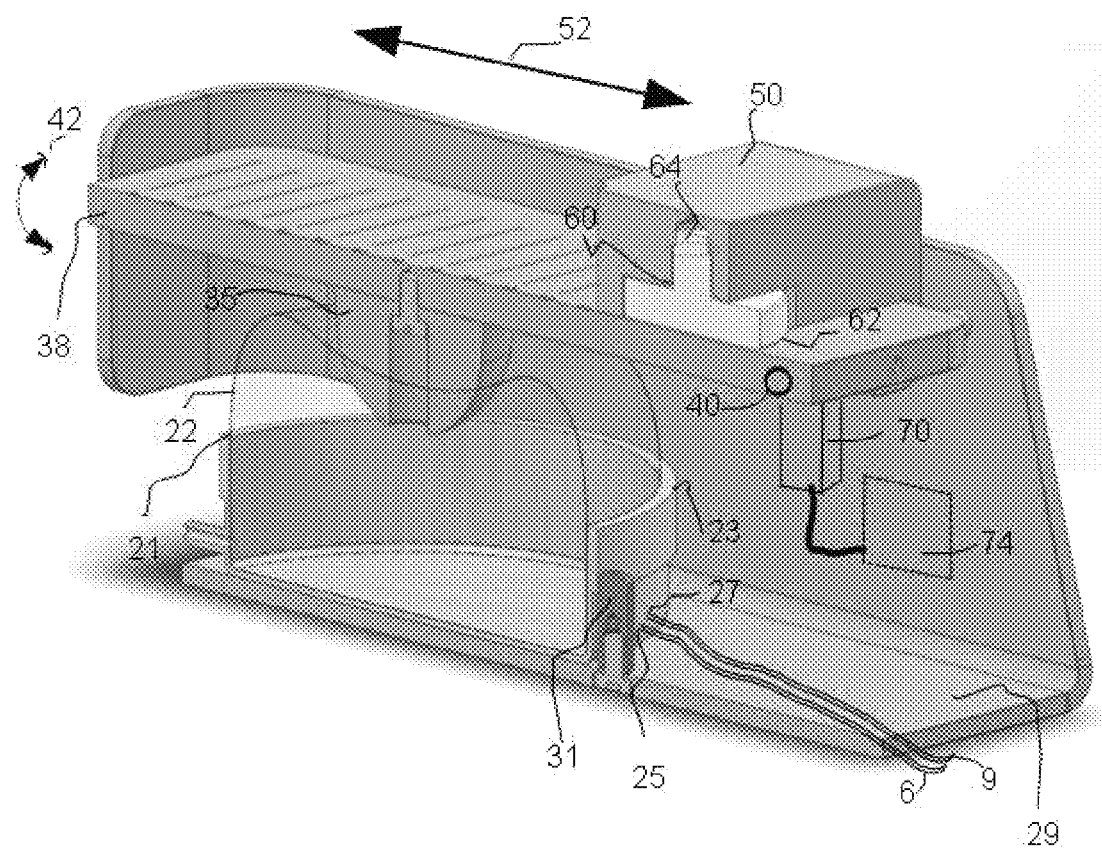
FIG. 2 represents a section of the regulator according to the invention.

FIG. 2 represents as a section the regulator according to the invention. It comprises a container 21 formed from a variable volume chamber 22 and a hub 23. The container 21 is provided with at least one first orifice 25 connected to the auxiliary hose 6 of the tube 1, such that, in use, the variable volume chamber of the pressure regulator and the sealing cuff 5 are in communication. A second orifice 27 is connected to the source 9. The container 21 is retained on the base 29 of the regulator in a correct position by means of three pins, one of which bearing the reference 31 is shown in FIG. 2. Preferably, the connections of the air pipes are made using LUER hubs.

Preferably, for hygiene reasons, the container 21 is produced in the form of a disposable element, for a single patient, such as a bag made of a flexible and waterproof material and of a similar shape to an infusion bag.

According to one aspect of the invention, the pipes connected to the cuff will be glued and not entered by force. Thus, air cut-offs that may be very damaging to the patient are avoided. Furthermore, to prevent incorrect connections of the auxiliary hoses, the various colors are allocated to the functions of the various pipes so that, the connection being performed correctly, continuity is noted in the colors.

In order to define accurately and consistently the pressure present inside the chamber 22, a piston 35 is used creating pressure on the top of the chamber 22. The piston 35 is dependent on a rod 38 that is able to pivot about an axis 40 as indicated by the double arrow 42. On this rod, a weight 50 can move according to the double arrow 52. The attachment of the weight on the rod will be explained later in the present description, According to the invention, the movement of the weight 50 may be blocked or locked such that an unexpected movement can be prevented. The blocking is obtained by means of a screw 60, the head 62 of which rubs against the surface of the rod and the threaded part 64 penetrates into the body of the weight 50. By maneuvering the screw head 62, given the fact that the weight 50 is held pressed against the rod 38, the blocking of the weight at a given position along the rod is thus obtained. The position of the weight sets the pressure of the air contained in the container 21 and thus, the pressure within the cuff 5.

According to another aspect of the invention, the rod 38 is combined with a movement detector 70 coupled to an electronic system which provides various pieces of information to, in particular, a display unit 74 such as the pressure and the history of the manipulations that have been performed by means of the respirator apparatus.

Figure 3:
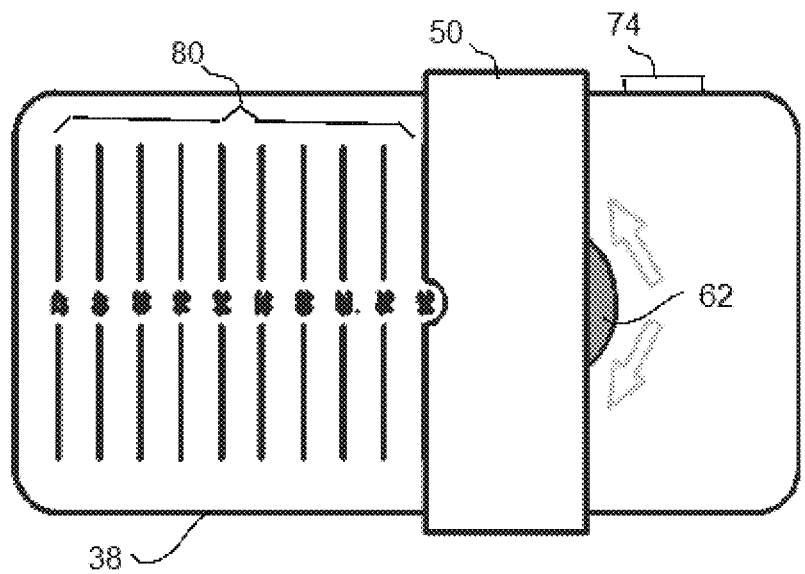
FIG. 3 represents a front perspective view of the pressure regulator according to FIG. 1.

FIG. 3 shows, top view, the rod 38 on which the weight is placed 50. FIG. 3 shows that a pressure index 80 is engraved on the face of the rod 38. The head of the locking screw is accessible such that it is possible for an operator to block and unblock the movement of the weight 50.

Figure 4:
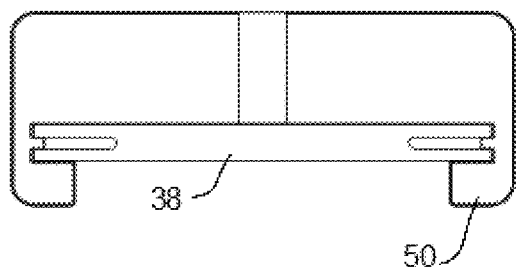
FIG. 4 shows a section of the weight with the rod.

FIG. 4 clearly shows that the weight 50 has a stirrup shape which fits tightly around the rod 38. In this way, the weight is secured to the rod 38 but the longitudinal movement thereof is rendered possible in unblocking position.

Figure 5:
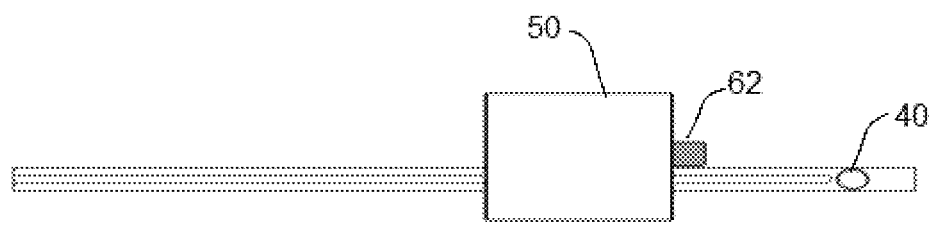
FIG. 5 shows a cross section of the rod.

FIG. 5 shows a cross-sectional view of the rod 38.

Figure 6:
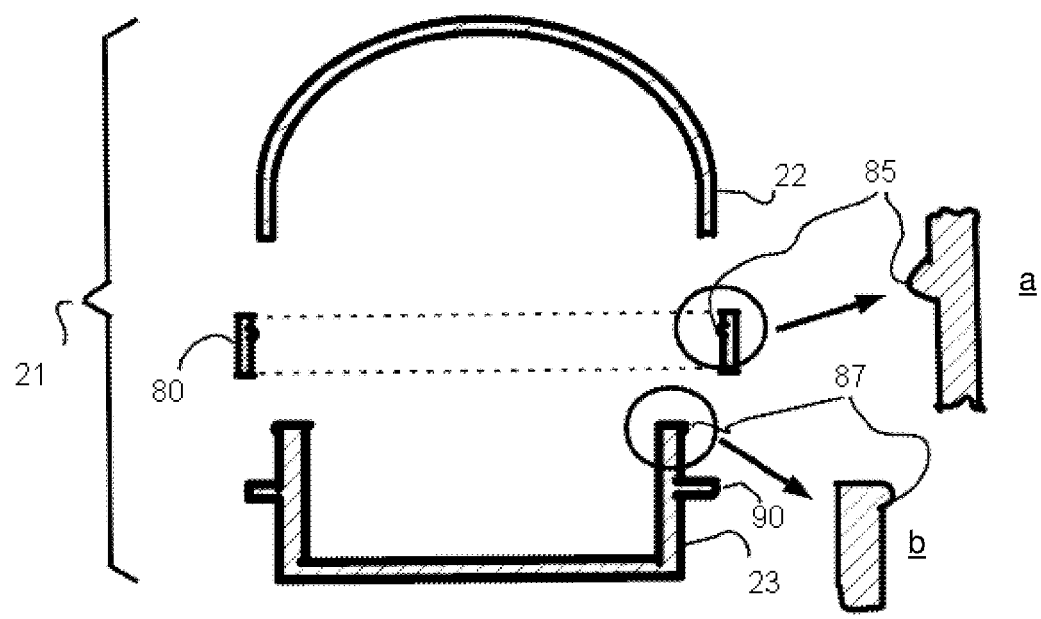
FIG. 6 shows, in a detached way, the constituent elements of an alternative embodiment of the container.
Figure 7:
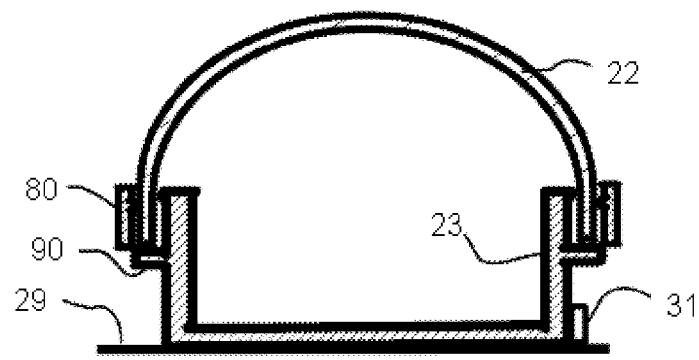
FIG. 7 shows the container of FIG. 6 after the assembly thereof.

According to one aspect of the invention, it is proposed as shown in FIGS. 6 and 7 a preferred embodiment of one embodiment of the container 21. The container is made of three elements, two of which have already been mentioned: the variable volume chamber 22 and the hub 23. The variable volume chamber 22 is produced from a flexible and transparent plastic material and slides along the upper edge of the hub 23. In order to provide a robust attachment, a ring 80 is provided which holds the variable volume chamber 22 tightly against the hub 23.

FIG. 6 shows in a separate way all of the elements 22, 23 and 80 not assembled. FIG. 7 shows the container 21 assembled, placed on the base 29 of the regulator.

In order to provide good attachment of the elements, a ring bead 85 is provided placed on the inner periphery of same. In a in FIG. 6, the bead is shown in greater detail. The bead 85 engages with a hub bead 87 located in the upper and outer part of the hub 23. This is shown in an expanded manner in b in FIG. 6. In this way, during the assembly of the chamber, the lower part thereof is wedged in a sealed way by the two beads 85 and 87. It is also provided a rim 90 protruding around the outer periphery of the hub 23 constituting a cleat for the ring 80 and the lower edge of the chamber 22.

The invention is of course not limited to the example described, given purely by way of example and many changes can be made easily by persons skilled in the art without departing from the scope of the invention.

The invention claimed is:

1. A system comprising:
a pressure regulator for an endotracheal tube,
a tube comprising:
a main pipe having a first end configured to be inserted into a trachea of a patient and a second end configured to be connected to a respirator apparatus;
an inflatable annular sealing cuff that surrounds the first end of the main pipe;
at least one auxiliary hose having a first end connected to the sealing cuff and a second end provided with a valve that can be connected to a compressed air source for inflating the sealing cuff;
a container defining a variable volume chamber having at least one first orifice to be connected to the auxiliary hose such that, in use, the variable volume chamber of the pressure regulator and the sealing cuff are in fluid communication;
a weight being movable along an articulated rod for adjusting the air pressure contained in the variable volume chamber, and consequently the air pressure contained in the sealing cuff;
a locking system for locking the weight to prevent unexpected movement of the weight.

2. The system according to claim 1 wherein, the variable volume chamber is formed from flexible plastic material and slides along an upper edge of a hub of the container resting on a base of the regulator.

3. The system according to claim 2 further comprising a ring that holds the variable volume chamber tightly against the hub.

4. The system according to claim 3 further comprising beads placed on peripheries of the hub and of the ring to wedge a lower edge of the chamber.

5. The system according to claim 1 wherein the locking system includes a screwable element provided with a friction head to be placed in blocking contact on one part of the rod by a rotational motion.

6. The system according to claim 1 further comprising a movement detector attached to the rod to provide a pressure indication to a management device for displaying on a screen the pressure indication and a history of various preceding operations.

7. The system according to claim 1 wherein the at least one auxiliary hose comprises an indicator to prevent connection errors.

8. The system according to claim 1 wherein connections of the at least one auxiliary hose are glued.

9. The system according to claim 1 further comprising a management device that engages with a screen for displaying at least one pressure indication and that includes memory devices to contain the history of use.

10. A breathing system comprising the system according to claim 1 and a respirator apparatus.

* * * * *